US007993844B1

(12) United States Patent
Sagripanti et al.

(10) Patent No.: US 7,993,844 B1
(45) Date of Patent: Aug. 9, 2011

(54) ARTIFICIAL CHIMERAS ENGINEERED TO SIMULATE MULTIPLE BIOLOGICAL THREAT AGENTS

(75) Inventors: Jose-Luis Sagripanti, Bel Air, MD (US); Monica Carrera, Buenos Aires (AR)

(73) Assignee: United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/873,825

(22) Filed: Sep. 1, 2010

Related U.S. Application Data

(62) Division of application No. 12/177,527, filed on Jul. 22, 2008, now Pat. No. 7,790,452.

(51) Int. Cl.
*C12Q 1/68* (2006.01)

(52) U.S. Cl. .......................................................... 435/6

(58) Field of Classification Search ........................ None
See application file for complete search history.

(56) References Cited

OTHER PUBLICATIONS

Carrera et al (Conference proceeding, NTIS Accession No. ADA481840, Edgewood Chemical Biological Center, Aberdeen Proving Ground, MD, USDGRDR0820, Nov. 1, 2006, pp. 1-9).*
Wei et al (Journal of Clinical Microbiology, 46(5):1734-1740, 2008).*

* cited by examiner

*Primary Examiner* — Patricia A Duffy
(74) *Attorney, Agent, or Firm* — Ulysses John Biffoni

(57) ABSTRACT

This invention provides safe, non-infectious chimeras that include the nucleic acid signature of most bacterial and viral biological threat agents. These chimeras mimic properties of threat agents and are useful as simulants to develop, evaluate, test, and train on nucleic acid-based biodetectors and diagnostic products of interest in biodefense, without the need for accessing or producing virulent agents.

3 Claims, 6 Drawing Sheets

```
                    ┌──────────────────┐
    ┌─────┐ ┌─────┐ │     ALL-G        │
    │  G  │ │  R  │ │  THREAT AGENTS   │
    │(Bru-│ │(Bru-│ │ DATABASE EXCEPT  │
    │cella│ │cella│ │      "G"         │
    │group│ │meli-│ │(excluding        │
    │  )  │ │tensis│ │  Brucella)      │
    └─────┘ │3198 │ └──────────────────┘
            │genes)│
            └─────┘
```

```
                    ┌──────────────────┐
                    │ BLAST (R) VERSUS │
                    │     (ALL-G)      │
                    └──────────────────┘
                             │
    ┌──────────────┐         ▼
    │  DESCARTED   │      ╱ FIRST ╲
    │    GENES     │◄────╱         ╲
    │ (639 GENES)  │     ╲SELECTION╱
    └──────────────┘      ╲       ╱
                             │
                             ▼
                    ┌──────────────────┐
                    │ GENES WITH NO HITS│
                    │      (NO)        │
                    │  (2559 GENES)    │
                    └──────────────────┘
                             │
    ┌──────────────┐         ▼
    │  G DATABASE  │──►┌──────────────────┐
    │    [G-R]     │   │ BLAST (NO) VERSUS│
    └──────────────┘   │     (G-R)        │
                       └──────────────────┘
                             │
    ┌──────────────┐         ▼
    │ NOT CONSERVED│      ╱ SECOND ╲
    │GENES DESCARTED│◄───╱          ╲
    └──────────────┘    ╲ SELECTION ╱
                         ╲         ╱
                             │
                             ▼
                    ┌──────────────────┐
                    │  CONSERVED GENES │
                    │     SELECTED     │
                    │  (2151 GENES)    │
                    └──────────────────┘
                             │
                             ▼
                    ┌──────────────────┐
                    │ LIST OF SELECTED │
                    │ GENES FOR EVERY  │
                    │   THREAT AGENT   │
                    └──────────────────┘
```

FIG. 1

| Order in the chimerical DNA | Organism or group | Preferred size in sample | Size in Simulant | Digested with EcoR1 | Digested with SmaI |
|---|---|---|---|---|---|
| 1 | Francisella tularensis | 230 | 100 | 37 | 29 |
| | | | | 63 | 71 |
| 3 | Burkholderia group | 260 | 115 | 37 | 29 |
| | | | | 78 | 86 |
| 5 | Rickettsia group | 290 | 130 | 37 | 29 |
| | | | | 93 | 101 |
| 7 | Coxiella burnetti | 310 | 145 | 76 | 68 |
| | | | | 69 | 77 |
| 9 | Brucella group | 330 | 160 | 77 | 75 |
| | | | | 83 | 85 |
| 10 | Escherichia coli O157:H7 group | 350 | 175 | 91 | 83 |
| | | | | 84 | 92 |
| 8 | Variola virus | 380 | 190 | 129 | 131 |
| | | | | 61 | 69 |
| 6 | Bacillus anthracis pXO1 | 150 | 205 | 118 | 110 |
| | | | | 87 | 95 |
| 4 | Bacillus anthracis pXO2 | 169 | 220 | 130 | 122 |
| | | | | 90 | 98 |
| 2 | Yersinia group | 200 | 235 | 153 | 145 |
| | | | | 82 | 90 |

FIG. 2

| Order in the chimerical DNA | Virus | Size in pathogen | Size in Simulant | Digest with EcoR1 | Digested with SmaI |
|---|---|---|---|---|---|
| 1 | Lassa | 245 | 118 | 80 / 38 | 89 / 29 |
| 3 | Yellow Fever | 268 | 128 | 40 / 38 | 49 / 29 |
| 5 | Ebola Zaire | 304 | 149 | 111 / 38 | 120 / 29 |
| 7 | EEEV | 321 | 160 | 102 / 58 | 111 / 49 |
| 9 | Junin | 355 | 180 | 118 / 62 | 127 / 53 |
| 11 | Marburg | 376 | 190 | 118 / 72 | 127 / 63 |
| 13 | Dengue | 511 | 210 | 121 / 89 | 130 / 80 |
| 12 | Crimean Congo | 549 | 220 | 116 / 104 | 125 / 95 |
| 10 | VEEV | 108 | 232 | 111 / 121 | 120 / 112 |
| 8 | Influenza | 138 | 256 | 124 / 132 | 133 / 123 |
| 6 | RVFV | 170 | 280 | 135 / 145 | 144 / 136 |
| 4 | Machupo | 200 | 292 | 141 / 151 | 150 / 142 |
| 2 | Actin (+) | 450 | 450 | 221 / 229 | 230 / 220 |

ARTIFICIAL CHIMERAS ENGINEERED TO SIMULATE MULTIPLE BIOLOGICAL THREAT AGENTS

RELATED APPLICATION

This application is a divisional of application Ser. No. 12/177,527, filed on Jul. 22, 2008, now U.S. Pat. No. 7,790,452.

FIELD OF THE INVENTION

This present invention includes the design and construction of non-infectious chimeras that include the nucleic acid signature of most bacterial and viral biological threat agents. One of the engineered chimeras simulates the biological threat agents whose genomes are DNA and the second engineered chimera simulates biological threat agents whose genomes are RNA. The chimeras of the present invention are also included in methods and devices of the present invention such as nucleic acid-based biodetectors and diagnostic products, and as simulants to allow the safe validation (and to compare) the performance of technologies, products, and devices used in biodefense, as well as in clinical detection and diagnosis of the said agents

BACKGROUND OF THE INVENTION

The threat of biological warfare has existed for centuries. By definition, biological warfare involves any deliberate use of disease to attack humans, plants, animals, or infrastructure. Biological weapons have been used only occasionally, but they have the potential to inflict great harm. Unlike the materials necessary to produce nuclear weapons, microorganisms, toxins, and viruses that are dangerous to human, animal, and plant life can be found abundantly in nature. The technology needed to turn these agents into weapons is less sophisticated than what is necessary to develop nuclear weapons. Furthermore, only a very small quantity of material is needed, much less than that needed to produce nuclear weapons, but could potentially cause a comparable death-toll.

Technology allows for some biological threat agents, which in their natural state pose only minimal dangers, to be genetically engineered into more threatening forms. Their availability in nature also changes, and science continues to discover new biological threat agents. The Center for Disease Control (CDC) and other agencies have compiled a list of the biological agents of greatest concern. They are segregated into categories, depending on a variety of factors.

Though the need to develop biological defense technologies to protect against the threat of terrorism is increasing, such biological defense technologies are hard to develop and test. Biological defense technologies are successful if they are able to detect the biological threat agent, inhibit biological threat agent contact with its host, inhibit biological threat agent growth, or kill the biological threat agent. Developing and testing biological defense technology in the presence of a biological threat agent poses serious hazards. Exposure of people working on defense technology, and/or the population at large, to a biological threat agent may result in serious injury or death. Methods allowing the safe development, testing, and training of biological defense technology are needed to minimize, or eliminate, the potential hazards associated with such technology development. However, the use of actual virulent threat agents is costly and risky. Furthermore, development and testing of technologies dealing with more than one threat agent face almost insurmountable difficulties in producing, storing, and employing more than one threat agent simultaneously.

The use of biological threat agents in the development, testing, and training of biological defense technology is impaired by safety issues, high cost, the need of special infrastructure and uncommon expertise. A simulant is an agent having biological and/or physical characteristics similar to a biological threat agent but when used in place of the biological threat agent is not harmful. Though the use of methods involving simulants is a good idea, very few simulants have been identified and are being used. In biodefense a few simulants, including spores of *Bacillus subtilis* (as surrogate of *B. anthracis*), *Pantoea agglomerans* (as surrogate of all vegetative threat bacteria) and the phage M13 (as surrogate of all threat viruses), are used in methods development, training, and testing and evaluation of biodefense countermeasures, and equipment. These simulants are totally inadequate to simulate threat agents on nucleic-acid based technologies, since *B. subtilis*, *P. agglomerans*, and M13 do not share genes with any of the actual threat agents that they are intended to mimic

SUMMARY OF THE INVENTION

Accordingly, it is an object of the present invention to meet the foregoing needs by providing safe methods for the development, testing, and training of biological defense technology. One embodiment of the present invention is a chimera comprising a plurality of segments, wherein each segment uniquely corresponds to a portion of the genome of a threatening biological agent wherein the genome is DNA. It is preferred that the threatening biological agent is selected from the group consisting of: *Bacillus anthracis*, *Yersinia* species, *Burkholderia* species, *Francisella* species, *Brucella* species, *Coxiella burnetii*, *Ricketsia* species, enterohemorrhagic *Escherichia* species, and variola virus and the chimera further comprising a nucleic acid sequence comprising SEQ ID NO.12. It is also preferred that the chimera of the present invention includes a segment having a DNA sequence derived from SEQ ID NOs: 1, 2, 3, 4, 5, 6, 7, 8, 9, 10, and 11.

Another embodiment of the present invention includes a chimera comprising a plurality of segments, wherein each segment uniquely corresponds to a portion of a genome of a threatening biological agent whose genome is RNA. It is preferred that the threatening biological agent is selected from the group consisting of: Eastern Equine Encephalitis Virus, Junin virus, Marburg virus, Dengue virus, Venezuelan Equine Encephalitis Virus, Crimean Congo virus, Influenza virus, Rift Valley Fever Virus, Machupo virus, Lassa virus, and Yellow Fever virus, and the chimera further comprising a nucleic acid sequence comprising SEQ ID NO.26. It is also preferred that this chimera of the present invention includes segments of DNA sequences derived from SEQ ID NOs: 13, 14, 15, 16, 17, 18, 19, 20, 21, 22, 23, 24, and 25.

Another embodiment of the present invention includes a vector comprising a chimera of the present invention. The vector may be a plasmid, a virus, a cosmid, or a yeast artificial chromosome. Preferably the vector is a plasmid or a virus.

Another embodiment of the present invention includes a method of testing a detection technology, comprising the steps of: (a) providing a sample containing the chimera of the present invention in lieu of a sample containing a biological threat agent; and (b) using said detection technology in accordance with normal or standard procedures to detect threat agent in the sample; and (c) determining the effectiveness of said detection technology in detecting a portion of the chimera. It is preferred that the detection technology comprises a nucleic acid probe capable of selectively hybridizing to at least a portion of a chimera of the present invention. It is also preferred that this method of the present invention also comprises the step of measuring a level of detectable signal.

In yet another embodiment of the present invention, the chimeras of the present invention may be used as positive controls when conducting assays for detection of biological threat agents in samples. For example, if ten different samples suspected of containing threat agent were being tested to detect a biological threat agent, an eleventh sample containing a chimera of the present invention could be tested concurrently to ensure that a positive test result is obtained.

BRIEF DESCRIPTION OF THE DRAWINGS

The accompanying drawings, which are incorporated in and constitute a part of this specification, illustrate embodiments of the present invention and, together with the description, explain the advantages, and principles, of the invention.

FIG. 1 Selection of Nucleic Acid Segments using Bioinformatics

FIG. 2 Design and Synthesis of Nucleic Acid Segments for Detecting Biological Threat Agents having DNA Genomes FIG. 3 Design and Synthesis of Nucleic Acid Segments for Detecting Biological Threat Agents having RNA Genomes FIG. 4 A Plasmid Containing the Chimera for Detecting Biological Threat Agents Having DNA Genomes.

FIG. 5 A Plasmid Containing the Chimera for Detecting Biological Threat Agents Having RNA Genomes FIG. 6 Confirmation of simulant construct by release of biothreat-agent specific bands by restriction enzyme digestion and gel-electrophoresis analysis

DETAILED DESCRIPTION OF THE INVENTION

Figure 6:
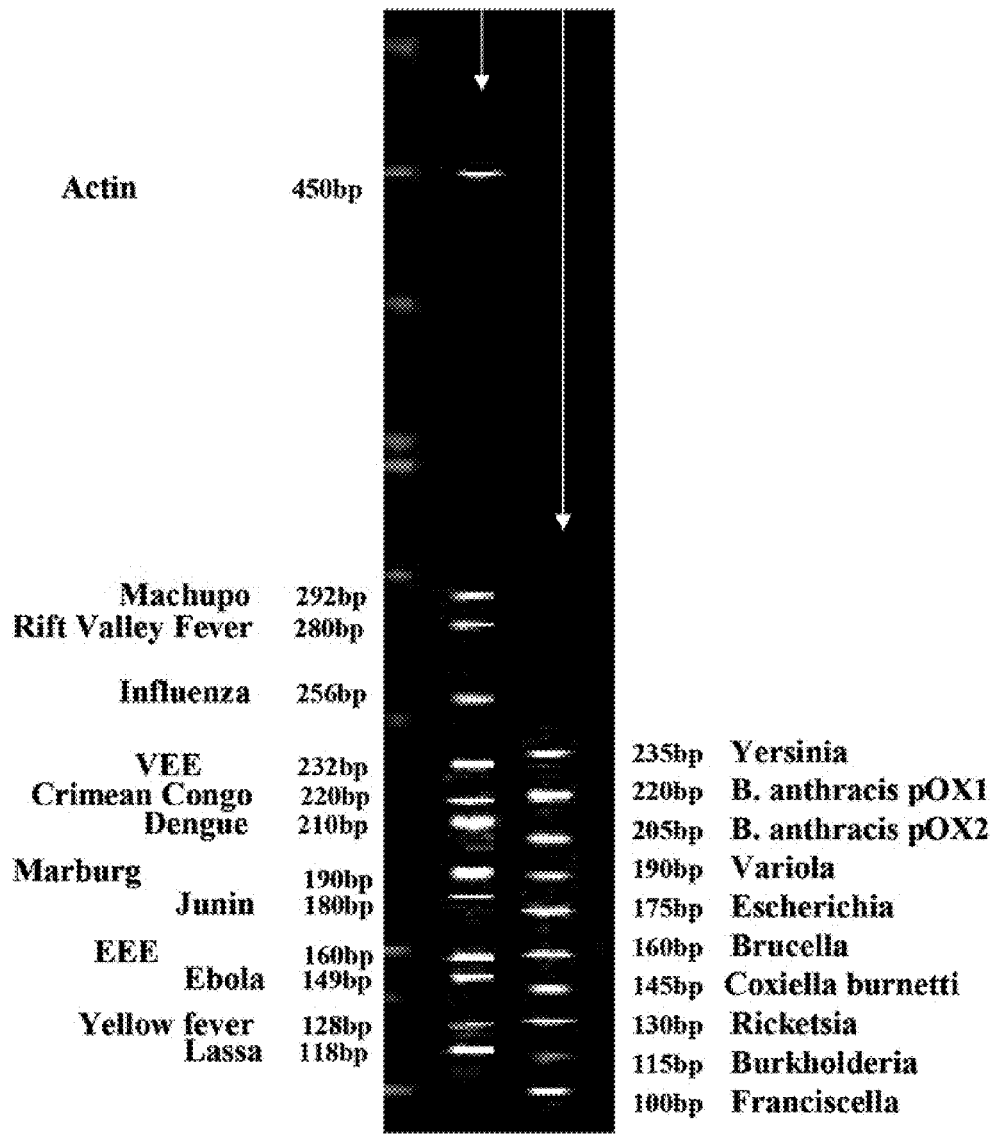

Reference will now be made to preferred embodiments of this invention. The current invention relates to biological threat agent simulants and to methods and products in which simulants replace biological threat agents during the development, testing, and/or training of biological defense technology. In order to better understand the invention, the following terms have been defined.

The term "biological defense technology" means a device, product and/or method able to detect a threatening biological agent, protect people, plants, livestock or other assets from contact with a threatening biological agent, and/or render harmless one or more threatening biological agents. Examples of biological defense technology include filters, masks, protective clothing, protective creams or gels, decontamination products and solutions, and devices or methods to detect and/or identify threat agents. A device includes a machine and/or equipment. A product includes a filter, gel, foam or other non-mechanical item. A method includes the use of a product and/or device.

The term "harmful" means resulting in injury, disease or death.

The term "inactivate" means to kill threat agent organisms, cells, spores or viruses and render them harmless or nonviable.

The term "virion" means a budded virus, or a virus not enmeshed in a polyhedrin matrix.

The term "simulant" means an agent having similar biological characteristics to a threatening biological agent but when used in place of the threatening biological agent is not harmful. The term includes one or more simulants and/or any combination of simulants.

The term "threatening biological agent" or "biological threat agent" means microorganisms, toxins, and/or viruses that are dangerous to human, animal, and/or plant life and as defined in this patent application. The term includes one or more threatening biological agents and/or any combination of threatening biological agents.

The term "virus threat agent" means a threatening biological agent that is a virus dangerous to human, animal, and/or plant life.

A simulant of the present invention is one or more agent(s), such as a nucleic acid sequence, preferably a DNA sequence that corresponds to one or more threatening biological agents. Such a simulant of the present invention takes the place of one or more threatening biological agents during the development, testing, and training of biological defense technologies.

Specifically, the simulant(s) of the present invention are chimeras; a genetic element made up of a plurality of nucleic acid segments, wherein each segment corresponds to the nucleic acid sequences of a threatening biological agent. The chimerical simulants are by design non-infectious to humans. Threatening biological agents are described within the Center for Disease Control (CDC) list of today's most dangerous biological agents, that is, within Category A, Category B, and/or Category C of the list. The CDC's list of the most dangerous biological agents includes organisms such as anthrax, plague, smallpox, tularemia, and viral hemorrhagic fevers.

The present invention specifically includes design and construction by genetic engineering of non-infectious chimeras that include the nucleic acid signature of most or all bacterial and viral biological threat agents. One embodiment of the present invention is chimeras that simulate biological threat agents whose genomes are DNA. Examples of biological threat agents whose genomes are DNA include: *Bacillus anthracis* (signatures from both virulent plasmids), *Yersinia* species, *Burkholderia* species, *Francisella* species, *Brucella* species, *Coxiella bumetii, Ricketsia* species, enterohemorrhagic *Escherichia* species, and variola virus (Smallpox). Another embodiment of the present invention is chimeras that simulate biological threat agents whose genome is RNA. Biological threat agents whose genome is RNA include members of the arenaviruses, filoviruses, alphaviruses, flaviviruses, and hantaviruses, more particularly the viruses: Ebola, Lassa, Yellow fever, Eastern Equine Encephalitis, Junin, Marburg, Dengue, Crimean-Congo, Venezuelean Equine Encephalitis, Rift Valley Fever, Machupo, and Influenza. The Chimeras once identified have been cloned into vectors such as viruses, plasmids or any other vehicle that allows the storage and amplification of the chimera sequences.

The risk of human injury or death is minimized when a simulant is used in the place of a threatening biological agent during the development, testing and/or training of a biological defense technology. Because the simulant and the threatening biological agent are selected to have similar characteristics (corresponding nucleic acid sequences) with the simulant being non-pathogenic, a simulant of the present invention may take the place of a threatening biological agent for product development, testing and evaluation, training, as positive controls, and wherever a non-infectious surrogate can beneficially replace actual threat agents. The results generated from such development, testing and/or training of a biological defense technology are then used to create new and effective biological defense technology, or improve existing biological defense technologies.

Discussion will now focus on examples of biological defense technology and their functions. Biological defense technology able to detect a threatening biological agent includes devices, products, and/or methods able to detect such agents in the air, in water, in food, in bodily fluids, or on solid surfaces. Detection of such agents in air generally consists of three steps: sample collection; sample processing; and sample analysis. Instrumentation accomplishing each step may be part of an integrated system, or samples may be collected, processed, and analyzed by separate systems (or by humans working with laboratory equipment). Some detection systems may sample the air passively, using currents in ambient air to cause airborne agents to move into the portion of the device that performs the analysis (in much the same way as a smoke detector detects smoke particles only when particle-laden air wafts into the interior of the detector).

Most active samplers that draw agents from air exploit one or more physical characteristics of the agents targeted for collection and contact with the biological defense technology. Such methods include but are not limited to the use of filters causing separation of particles from air based on size. Air can be drawn by fans (or other methods of moving air) and passed through filters designed with pore sizes small enough to retard the passage of airborne particles that carry virions. Another class of samplers accelerates air (and therefore airborne agents) and increases the momentum of airborne agents, then passes such particles through a path in the instrument in such a way that the momentum of particles causes them to leave the airstream and impact on a surface or into a fluid where they are arrested. Such devices are often said to work by "impaction" and may be called an "impaction sampler". Conceivably, air samplers for threatening biological agents could also work by adsorption (an adsorption sampler), in which air is passed through a column filled with a porous substrate that has an affinity for the threatening biological agents based on one or more methods, including but not limited to: charge, the complementarily of molecular surface structures (including but not limited to an antibody-antigen interaction), relative hydrophobicity/hydrophilicity. Sample collection from liquid samples employs many of the same techniques listed above.

Sample collection from surfaces usually employs the use of a swab (often composed of cotton, but can be any of a large number of materials) or other material or device that is wiped over a surface with the intent that particles on the surface adhere to the swab. Samples from food can involve the use of swabs or a more frequently a disruption of a portion of the food into a proper media and further analysis. Collection of samples from bodily fluids, including sputum, bronchial swabs or lavage, urine, feces, spinal fluid, or blood, is well known to those involved in the art.

The term "sample processing" refers to methods of preparing a sample for analysis, which is making the threatening biological agent or components thereof such as membrane proteins, DNA, and/or RNA accessible (able to come in contact with) to a detection device so that the detection device is able to detect the presence of a molecule characteristic to a biological threatening agent. Such molecules include RNA, DNA, protein and/or lipid (i.e., content and/or composition). Typically, the integrity of a threatening biological agent's cell, spore, or virion is disrupted by chemical, enzymatic, electrical, mechanical and/or other means. For example, such disruption means may cause the release of nucleic acids from a threatening biological agent and make them available for methods of analysis that rely upon nucleic acid sequence information for detection and identification. Another reason a sample might require preparation is that a molecule characteristic of a threatening biological agent may have to be modified or combined with other compounds before analysis. An example of this kind of modification is the derivatization of small molecules before gas chromatographic analysis.

A biological defense technology may detect a nucleic acid signature of a threatening biological agent. Nucleic acid hybridization is used to detect a biological agent by contacting a target nucleic acid (i.e. the nucleic acid signature specific to a particular threatening biological agent or simulant) with a nucleic acid probe capable of selectively hybridizing to at least a portion of the target nucleic acid sequence. The chimeras of the present invention are nucleic acid and can be detected by nucleic acid probes. Nucleic acid hybridization methods applicable to this invention are described in Sambrook et al. The detection may also occur by polymerase chain reaction (PCR) as described in Barlett et al.

PCR is typically used in nucleic acid based detection methods. Small amounts of biological threat agents may be present in a suspect sample and the corresponding low amount of nucleic acid sequences of the biological threat agents may have to be amplified to be detected. In order to amplify the nucleic acid sequences of a biological threat agent, lysis of the cell, or virus particle, preferably occurs by conventional methods. Then the nucleic acid sequences present in the sample are heated so that it becomes denatured to form single stranded nucleic acid sequences. The denatured nucleic acid sequences are cooled and nucleic acid probes are annealed. The probes are specific to the biological threat agent thought to be in the sample. Taq or equivalent polymerase binds the 3' end of each nucleic acid probe annealed to nucleic acid sequences and extends each of these primers in the 5' to 3' direction along the nucleic acid sequences. PCR typically results in a doubling of the number of copies of nucleic sequences after each round of DNA synthesis and a geometric increase in number of copies after each reaction cycle. The chimera in the present invention can be used to test different primers (probes), conditions, specificity, and sensitivity to be used in the PCR amplification method, or nucleic acid based detection methods. The PCR product (amplified nucleic acid sequence) can be observed afterwards by separation of the DNA by agarose gel electrophoresis, capillary electrophoresis, real time fluorescence, or other detection methods known to those familiar in the art.

Some biological defense technology must be able to detect very small amounts of threatening biological agents in a relative large amount of material; for example, a small number of anthrax spores in a thick layer of dust on top of a computer. Such non-pathogenic material collected with a threatening biological agent must be removed before a threatening biological agent may be detected and identified. Methods for the removal of such non-pathogenic materials may include, but are not limited to, purification by means of ligand-receptor affinity (of which antibody-antigen affinity or nucleic hybridization are possible examples).

Other types of decontamination technologies include but are not limited to methods and devices that transmit radiant energy (such as ultraviolet radiation) to threatening biological agent cells, spores, or virions in such a way that the absorbance of the radiant energy disrupts threatening biological agent cells, spores, or virions in the ways mentioned above. Another class of decontamination technology includes methods or devices that generate aerosols or gaseous emissions of substances that inactivate threatening biological agent cells, spores, or virions in the ways described above. An example of such a technology is a vaporous hydrogen peroxide (VHP) generator. Hydrogen peroxide vapors, chlorine dioxide, paraformaldehyde vapors, or combinations thereof, are capable of penetrating the interiors of equipment and destroying threatening biological agent cells by chemically (oxidatively or otherwise) modifying small or macromolecules of threatening biological agent cells, spores, or virions so that they are no longer viable or able to cause disease.

A simulant of the present invention is a chimera containing segments of nucleic acid sequences, which is safe when in contact with humans and is able to take the place of a biological threat agent, preferably during the development, testing, and training of biological defense technology.

EXAMPLES

Example 1

Design and Synthesis of a Nucleic Acid Segments for Detecting Biological Threat Agents having DNA Genomes A single molecule chimera was made of DNA segments, each segment corresponding to the nucleic acid sequences of a biological threat agent having a DNA genome. The segments were identified using a novel bioinformatics approach. As shown in FIG. 1, this bioinformatics approach has multiple steps and uses computational tools to search and select non-infectious signature sequences corresponding to bacterial and viral threat agents whose genome is DNA, including *Bacillus anthracis, Yersinia pestis, Coxiella Burneti, Brucella* sp., *Francicella tularensis*, Entherohemorragic *E. coli*, O157: H7, *Burkholderia mallei, Burkholderia pseudomallei* and Variola virus (smallpox virus).

Once these nucleic acid sequences (or segments of the chimera) were identified, each segment was then prepared by PCR amplification. Synthetic chimeras were designed to produce PCR amplicons of different sizes than the amplified fragments from the original pathogenic genome (to identify any false positives).

Segments of the sizes shown in FIG. 2 were chosen to create the chimera for detecting Biological Threat Agents having DNA genomes. Added to each fragment were two restriction sites in the middle of the sequence (EcoRI-GAATTC- and SmaI-CCCGGG-). These enzymes won't cut the amplified segments from the microbial genomes; therefore the enzymes can be used to digest these segments in case of suspected contamination with the simulant. When the simulant amplicons were digested with internal restriction enzymes, two small fragments were obtained. (see right two columns in FIG. 2) For example, the *Francisella tularensis* simulant amplicon was a size of 100 bp and was digested by EcoR1 into two fragments of 37 bp and 63 bp were obtained. The corresponding fragment in the threat agent *Francisella tularensis* is 230 bp and is not digested by EcoR1.

Based on the bioinformatics study described in FIG. 1 and the primers (underlined in bold below) designed from segment sequences using the FastPCR software, DNA segments were selected as follows:

*Francisella* Segment
[SEQ ID NO.1]
GGATCCGACAAGCTTATGGCTTTGCAGCCACTTTT-
GCAATCGCTGTGTGAGCCCGGGCAGCGAATTCCC-
ATTTAGATTTTTTTGAATATGCTTGTAAAGACCGAG-
GCTCAGAACTAATCGCAGCTACAGCACAAG

*Yersinia* Segment
[SEQ ID NUMBER:2]
GGATCCTGAAAGCTTGCTGGGGCGAACCCACCTC-
ATTGGCTATGGCGGCGTCGCCTGTCACGTCCTGTT-
TGAGTGGGATAAACGCCACGATGAGTTCGATCTCG-
CCATACTGGAGAAAGCATGGAACCAGCTCATCGCA-
CGCCACGATATGTTGCGTATGGTGGTTGCCCGGGG-
CCTGAATTCTGACGATCCTCATTATGTCAATATCGG-
TACGGTGTTAGACAACGCCGACTGACGCCGGAGTA-
TCACATCCCGCGTGACGATCTGCGC

*Burkholderia* Segment
[SEQ ID NUMBER:3]
GGATCCATGAAGCTTCATTCGTCTTTGCCATTGCCC-
TGTCATTTGCCGCAGCCCGGGTGCTGAATTCGTCA-
GCAATGCGAAATTTACATCCCTACGCGAGCCTTTT-
GTTTTTACCGACCTGAGTCTGTTCAGTCAGTTGTTC-
TCGCACCC pXO2 *B. Anthracis* Segment
[SEQ ID NUMBER:4]
GGATCCCTCAAGCTTTTACACGTTTTGCTGACCAAT-
CTAAGCCTGCGTTCTTCGTAAATGGTTTTGCAGCG-
AATGATCCCTCATCAACATTACGTATTTGGGAACGT-
GTGGATGATTTTGGATATAGTAATCTAGCTCCAATT-
GCCCGGGAGATGAATTCTACATCTGCGCGAATGAT-
ATATTGGTTTACTGACGAGGAGCAACCGATTAAGC-
GCCGTAGCGTTGATCGTACTGAGCAGTTTGCTAGG-
GATGTTT

*Rickettsia* Segment
[SEQ ID NUMBER:5]
GGATCCGGAAAGCTTAGCTGGTATCGCTTATTTTAG-
AGGTTATAGAGTTCGCCCGGGTAGTGAATTCGTAA-
ACCTTTATTTTTTGATCTTAATATTTCTACTAGAACC-
CAAAACGTATCCCAAGTTCAAAGAGCTTTACTTTT-
ACCTCAAGAAGTAATACAGTTA pXO1 *B. Anthracis* Segment
[SEQ ID NUMBER:6]
GGATCCTCTAAGCTTGAAAAAGGATTGGATTTCAA-
GTTGTACTGGACCGATTCTCAAAATAAAAAAGAA-
GTGATTTCTAGTGATAACTTACAATTGCCAGAATTA-
AAACAAAAATCTTCGAACTCAAGAAAACCCGGGG-
AAAGAATTCTCATCTCCTGAAAAATGGAGCACGGC-
TTCTGATCCGTACAGTGATTTCGAAAAGGTTGGAC-
CTACGGTTCCAGACCGTGACAATGATGGAAT.

*Coxiella* Segment
[SEQ ID NUMBER:7]
GGATCCACTAAGCTTCGGATTGTTACCCAACGAAA-
CCTTGCGTGAGGCATTGAATCGGGAATTAGATGAA-
GAAGTGG GACTGAGTCCTCACCCGGGTA|CAGAA-
TTCCAATGGCGGTGGGTTGATTATTGGTATCCGGT-
GGACCACGTCGTTGAGTTTAAGCGAGACGTTTATC-
AGAAAGT

*Variola* Segment
[SEQ ID NUMBER:8]
GGATCCATAAAGCTTCGGAAGAGATGCAGCACCGT-
ATACACCACCCAATGGAATCATTAGTATACTCTACA-
CCTTATCCTCAGACACAGATATCTAAAAAAATAGGT-
GATGATGCAACTCTATCATGTAGTAGAAATAATATA-
CCCGGGACGTGAATTCCAAACAAAATGTGGAATA-
GGATACGGAGTATCCGGACACACGTCTGTTGGAGA-
CGTCATCTGTTCT

*Brucella* Segment
[SEQ ID NUMBER:9]
GGATCCTAGAAGCTTAATTGTGGGCCGATGGCGTC-
ATCCATGTGCTGGGTGTCGGGCTGGCGCTTGCCGG-
TGCCATTGCCATGCTGTTCTATTTCCTCCCGGGAAT-
CGAATTCTATGGGCGACCGCGCGCTGCCCCTGCTG-
CTGTTCGTGTGGAGCGTGGCTTTCGTCGGCATCAT-
GCTCAAACTGTTCATGCCG

*Escherichia* Segment
[SEQ ID NUMBER:10]
GGATCCCTGAAGCTTGCGCGCTAACGCAGGCCTG-
AACTCATCGTCGGATGAATTACAGGCCCAGACGCG-
TATTGCCGGAATGCGCTCAACGCTGGAGCAATATC-
ACCCGGGGCACGAATTCAAGCGCAATACTGGCCA-

ACGCTCAGTATTCAGGGGGGTAAAACGCGCTACCA-
GACCAGCGACCGCTCGTATTGGGATGATCAGCTAC-
AA

Figure 4:
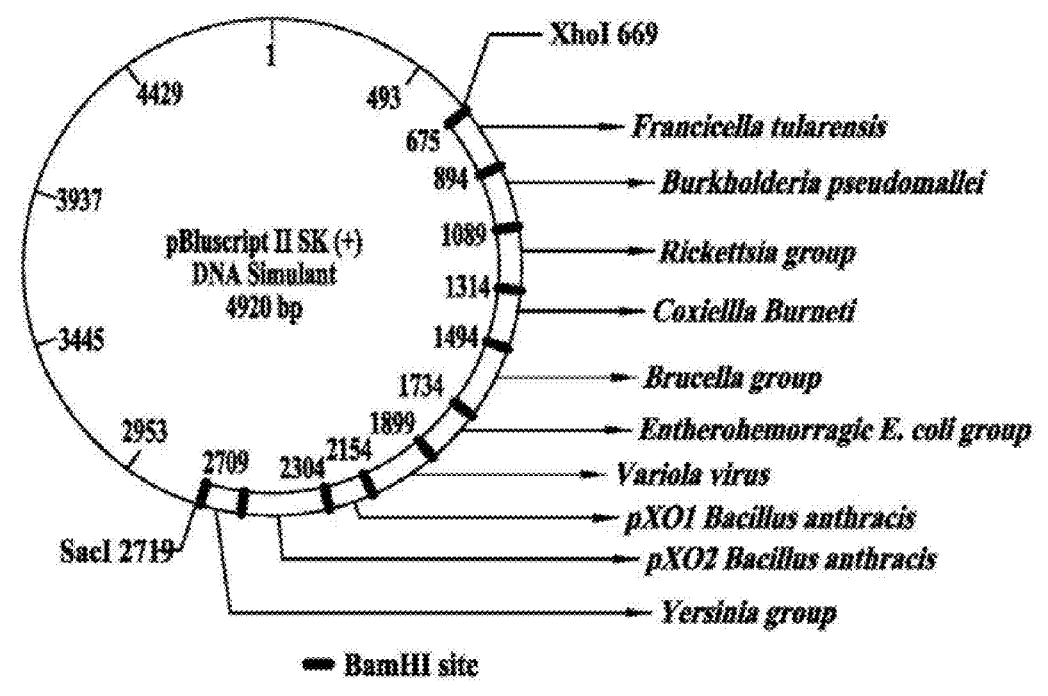

Smallpox Segment
[SEQ ID NUMBER: 11]
TCATTAGTATACTCTACACCTTATCCTCAGACACAG-
ATATCTAAAAAAATAGGTGATGATGCAACTCTATCA-
TGTAGTAGAAATAATATA A chimera able to mimic many different types of biological threat agents was created by DNA synthesis and the joining of the above-identified segments.
The whole chimera sequence for DNA genome threat agents is SEQ ID NUMBER: 12.
[SEQ ID NO: 12]
GGATCCGACAAGCTTATGGCTTTGCAGCCACTTTT-
GCAATCGCTGTGTGAGCCCGGGCAGCGAATTCCC-
ATTTAGATTTTTTTGAATATGCTTGTAAAGACCGAG-
GCTCAGAACTAATCGCAGCTACAGCACAAGGGATC-
CTGAAAGCTTGCTGGGGCGAACCCACCTCATTGGC-
CTATGGCGGCGTCGCCTGTCACGTCCTGTTTGAGT-
GGGATAAACGCCACGATGAGTTCGATCTCGCCATA-
CTGGAGAAAGCATGGAACCAGCTCATCGCACGCC-
ACGATATGTTGCGTATGGTGGTTGCCCGGGGCCTG-
AATTCTGACGATCCTCATTATGTCAATATCGGTACG-
GTGTTAGACAACGCCGACTGACGCCGGAGTATCAC-
ATCCCGCGTGACGATCTGCGCGGATCCATGAAGCT-
TCATTCGTCTTTGCCATTGCCCTGTCATTTGCCGCA-
GCCCGGGTGCTGAATTCGTCAGCAATGCGAAATTT-
ACATCCCTACGCGAGCCTTTTGTTTTTACCGACCTG-
AGTCTGTTCAGTCAGTTGTTCTCGCACCCGGATCC-
CTCAAGCTTTTACACGTTTTGCTGACCAATCTAAGC-
CTGCGTTCTTCGTAAATGGTTTTGCAGCGAATGATC-
CCTCATCAACATTACGTATTTGGGAACGTGTGGATG-
ATTTTGGATATAGTAATCTAGCTCCAATTGCCCGGG-
AGATGAATTCTACATCTGCGCGAATGATATATTGGT-
TTACTGACGAGGAGCAACCGATTAAGCGCCGTAGC-
GTTGATCGTACTGAGCAGTTTGCTAGGGATGTTTG-
GATCCGGAAAGCTTAGCTGGTATCGCTTATTTTAGA-
GGTTATAGAGTTCGCCCGGGTAGTGAATTCGTAAA-
CCTTTATTTTTTGATCTTAATATTTCTACTAGAACCC-
AAAACGTATCCCAAGTTCAAAGAGCTTTACTTTTA-
CCTCAAGAAGTAATACAGTTAGGATCCTCTAAGCT-
TGAAAAAGGATTGGATTTCAAGTTGTACTGGACCG-
ATTCTCAAAATAAAAAAGAAGTGATTTCTAGTGAT-
AACTTACAATTGCCAGAATTAAAACAAAAATCTTC-
GAACTCAAGAAAACCCGGGGAAAGAATTCTCATC-
TCCTGAAAAATGGAGCACGGCTTCTGATCCGTACA-
GTGATTTCGAAAAGGTTGGACCTACGGTTCCAGAC-
CGTGACAATGATGGAATGGATCCACTAAGCTTCGG-
ATTGTTACCCAACGAAACCTTGCGTGAGGCATTGA-
ATCGGGAATTAGATGAAGAAGTGGGACTGAGTCCT-
CACCCGGGTACAGAATTCCAATGGCGGTGGGTTGA-
TTATTGGTATCCGGTGGACCACGTCGTTGAGTTTAA-
GCGAGACGTTTATCAGAAAGTGGATCCATAAAGCT-
TCGGAAGAGATGCAGCACCGTATACACCACCCAAT-
GGAATCATTAGTATACTCTACACCTTATCCTCAGAC-
ACAGATATCTAAAAAAATAGGTGATGATGCAACTCT-
ATCATGTAGTAGAAATAATATACCCGGGACGTGAAT-
TCCAAACAAAATGTGGAATAGGATACGGAGTATCC-
GGACACACGTCTGTTGGAGACGTCATCTGTTCTGG-
ATCCTAGAAGCTTAATTGTGGGCCGATGGCGTCAT-
CCATGTGCTGGGTGTCGGGCTGGCGCTTGCCGGTG-
CCATTGCCATGCTGTTCTATTTCCTCCCGGGAATCG-
AATTCTATGGGCGACCGCGCGCTGCCCCTGCTGCT-
GTTCGTGTGGAGCGTGGCTTTCGTCGGCATCATGC-
TCAAACTGTTCATGCCGGGATCCCTGAAGCTTGCG-
CGCTAACGCAGGCCTGAACTCATCGTCGGATGAAT-
TACAGGCCCAGACGCGTATTGCCGGAATGCGCTCA-
ACGCTGGAGCAATATCACCCGGGGCACGMTTCAA-
GCGCAATACTGGCCAACGCTCAGTATTCAGGGGGG-
TAAAACGCGCTACCAGACCAGCGACCGCTCGTATT-
GGGATGATCAGCTACAAAAGCTTAGAGGATCC A plasmid map comprising the whole chimera is shown in FIG. 4.

Example 2

Design and Synthesis of a Nucleic Acid Segments for Detecting Biological Threat Agents having RNA Genomes The strategy used to identify nucleic acid segments unique to Biological Threat Agents was different than that used in Example 1. The reason is that there is a higher probability of finding a unique DNA in larger bacterial genomes (Example 1) than in smaller viral genomes due to the significant disparity in genomic size between bacteria and viruses. Smaller viral genomes (Example 2) have been sequenced completely, unlike bacterial genomes requiring the need of large sequencing efforts. To obtain segments, or conserved regions of nucleic acid, among all isolates of one viral species, the genome sequences from all available isolates were aligned using ClustalW software (Thompson, J. D. et at 1997). The selection of possible primer sequences was performed manually looking at the alignments. This analytical approach was used to determine target nuclei acid sequence representing several RNA virus whose genome is RNA, Including but not limited to, nucleic acids in VEEV (Venezuelan Equine Encephalitis Virus), Influenza virus, Rift Valley Fever Virus, Machupo virus, Lassa virus, Yellow Fever virus, Ebola Zaire virus, Eastern Equine Encephalitis Virus, Junin virus, Marburg virus, Dengue virus, Crimean Congo virus.

Primer sequences were then selected manually by looking at the sequence alignments. Then Fast PCR was used as described in Example 1.

The following DNA Sequences were selected, based on the manual selection described above, and primers (underlined in sequences below) were designed from segment sequences using the FastPCR software for purposes of designing and chemically synthesizing the whole chimera as follows:
Restriction Sites:
GAATTCTACCCCGGG EcoRI/SmaI (intrafragments sites)
AAGCTTCGCGGATCC HindIII/BamHI (interfragments sites)
Ebola Segment
[SEQ ID NUMBER:13]
AAGCTTCGCGGATCCCGGCAATTGCACTCGGAGTC-
GCCACAGCACACGGGAGTACCCTCGCAGGAGTAA-
ATGTTGGAGAACAGTATCAACAACTCAGAGAGGCT-
GCCACTGAGGCTGAGAAGCAAGAATTCTACCCCG-
GGGTGCTGCGTCACTGCCCAAAACAAGTGGA
EEEV Segment
[SEQ ID NUMBER:14]
AAGCTTCGCGGATCCTTTACTTGTCTGCGGCGCCT-
TGGGCGCCGTAGTCGAACGCCCAGGTTATGCACCC-
GTTCACCTACAGATACAGCTGGTTAATACCAGGATA-
ATTCCATCAAGAATTCTACCCCGCGACAGGTGTTTA-
CCCATTCATCTGGGGAGGAGCCTACTGCTTCTGCG-
AC
Junin Segment
[SEQ ID NUMBER:15]
AAGCTTCGCGGATCCGCACCTCTGATCCAGACAT-
GTAGTCGACCCTTAACTTTGACATCAAATCCACAT- GATGGATTTGATTTGCATATGCCATCAAGAAATATC-
TTAGACCTTGTAAAAATGTCTGGTTCCGAATTCTAC-
CCCGGGCCCATTGATGGATAGATAGATAGAATAGC-
ACCTTGACTTCTCACCTGTTTTT Marburg Segment
[SEQ ID NUMBER:16]
AAGCTTCGCGGATCCATGAAGTTGCTAGTTTCAAG-
CAGGCGTTGAGCAACCTAGCCCGACATGGAGAATA-
CGCACCGTTCGCACGGGTTCTGAATTTATCAGGGA-
TTAACAACCTCGAACATGGACTCTATCGAATTCTAC-
CCCGGGTTCAGAAAACTGAAATCACACACAGTCA-
GACACTAGCCGTCCTCAGCCAGAAACGAGAAAAA Dengue Segment
[SEQ ID NUMBER:17]
AAGCTTCGCGGATCCTTTCAATATGCTGAAACGCG-
AGAGAAACCGCGTGTCAACTGTTTCACAGTTGGC-
GAAGAGATTCTCAAAAGGATTGCTTTCAGGCCAA-
GGACCCATGAAATTGGTGATGGCTTTTATAGCGAA-
TTCTACCCCGGGTTATGTGAGGACACAATGACCTA-
CAAATGCCCCGGATCACTGAGACGGAACCTGAA-
GACATTGACTGTTGGTGCAATG VEEV Segment
[SEQ ID NUMBER:18]
AAGCTTCGCGGATCCTAGTTAGTTGCGACGGGTAC-
GTCGTTAAAAGAATAGCTATCAGTCCAGGCCTGTA-
TGGGAAGCCTTCAGGCTATGCTGCTACGATGCACC-
GTTAAAAGAATAGCTATCAGGAATTCTACCCCGGG-
GGCTATGCTGCTACGATGCACCGTTAAAAGAATAG-
CTATCAGTCCAGGCCTGTATGGGAAGCCTTCAGGC-
TATGCTGCTACGATGCACCGCGAGGGATTCTTGTG-
CTGCAA Crimean Congo Segment
[SEQ ID NUMBER:19]
AAGCTTCGCGGATCCAATTGATGATGAGCATGTC-
AGGCATTGATTGTATAAAATATCCCACAGGGCAGC-
TTATCACCCATGGAAGAGTGAGTGCAAAACATAAC-
GATGGGAACCTGAAAGATAGAAGCGAGAATTCTAC-
CCCGGGAACCTGTGCCCTTTCAGGTTGACTGTATA-
TTGTTCAAAGAAGTGGCAGCTGAATGCATGAAGA-
GGTACATTGGCACACCTTATGAGGGAATTGT Influenza Segment
[SEQ ID NUMBER:20]
AAGCTTCGCGGATCCAAACCATTTGAATGGATGTC-
AATCCGACTCTACTGTTCCTAAAGGTTCCAGCGCA-
AAATGCCATAAGCACCACATTCCCTTATACTGGAGA-
TCCTCCATACAGCCATGGAACAGTCTACTGTTGAAT-
TCTACCCCGGGTGGAACAGTCTACTGTTCCTAAAG-
GTTCCAGCGCAAAATGCCATAAGCACCACATTCCC-
TTATACTGGAGATCCTCCATACAGCCATGGAACAGG-
AACAGGATACACCATGGACACAGTCAA RVFV Segment
[SEQ ID NUMBER:21]
AAGCTTCGCGGATCCTTATGAGTGCACTGCTCAGT-
ACGCCAATGCCTATTGTTCACATGCTAATGGGTCA-
GGGATTGTGCAGATACAAGTATCAGGGGTCTGGAA-
GAAGCCTTTATGTGTAGGGTATGAGAGAGTGGTTG-
TGAAGAGAGGAATTCTACCCCGGGACATGCTAATG-
GGTCAGGGATTGTGCAGATACAAGTATCAGGGGTC-
TGGAAGAAGCCTTTATGTGTAGGGTATGAGAGAGT-
GGTTGTGAAGAGAGAACTCTCTGCCAAGCCCATCC-
AGAGAGTTGAGCCTTGCAC Machupo Segment
[SEQ ID NUMBER:22]
AAGCTTCGCGGATCCTTCATTCATCATGTCTAAAGC-
AATGCAGACATCCAGAAATTTTAGCCTCCCGCTATC-
CATTGTTCTGCTGACCTGAAGATCATTCATAAATGG-
AGTCAAGTGTTCGTCAAAAAGAACTGGATAATTTC-
TCCTTATAGATTGAATTCTACCCCGGGTCTGCTGAC-
CCTGAAGATCATTCATAAATGGAGTCAAGTGTTCG-
TCAAAAAGAACTGGATAATTTCTCCTTATAGATTGC-
AGAACATGGTTCATTCCCAGTTGGTCTTCAATTTGT-
CTCACCACTTTAGGCTTCACAGCCCA Lassa Segment
[SEQ ID NUMBER:23]
AAGCTTCGCGGATCCTTATCCTGGGTGACCACTTC-
ATTTTGGTTGATGCTAAGTCGCTCATAAATGGCAG-
TATGTGTTTTTCAAATACAGATGGGAATTCTACCCC-
GGGAAGACCCATGCACCCAGTTCTATTGCAG Yellow Fever Segment
[SEQ ID NUMBER:24]
AAGCTTCGCGGATCCTGCTAAGCTGTGAGGCAGTG-
CAGGCTGGGACAGCCGACCTCCAGGTTGCGAAAA-
ACCTGGTTTCTGGGACCTCCCACCCCAGAGTAAAA-
GAATTCTACCCCGGGCAGTTTGCTCAAGAATAAGC-
AGACCTTT Actin Segment (450 pb)
[SEQ ID NUMBER:25]
AAGCTTCGCGGATCCGCGTCCGCCCCGCGAGCAC-
AGAGCCTCGCCTTTGCCGATCCGCCGCCCGTCCAC-
ACCCGCCGCCAGCTCACCATGGATGATGATATCGC-
CGCGCTCGTCGTCGACAACGGCTCCGGCATGTGC-
AAGGCCGGCTTCGCGGGCGACGATGCCCCCGGG-
CCGTCTTCCCCTCCATCGTGGGGCGCCCCAGGCAC-
CAGGGCGTGATGGTGGGCATGGGTCAGAAGGATT-
CCGAATTCTACCCCGGGTATGTGGGCGACGAGGCC-
CAGAGCAAGAGAGGCATCCTCACCCTGAAGTACCC-
CATCGAGCACGGCATCGTCACCAACTGGGACGAC-
ATGGAGAAAATCTGGCACCACACCTTCTACAATGA-
GCTGCGTGTGGCTCCCGAGGAGCACCCCGTGCTG-
CTGACCGAGGCCCCCTGAACCCCAAGGCCAACC-
GCGAGAAGATGACCCAGATCATGTTTGAGACCTTC-
AA These segments were then joined together to form a chimera to mimic many different types of biological threat agents whose genome is RNA. DNA synthesis was used to create the whole chimera based on the joining of segments. The entire chimera sequence for threat agents having RNA genomes is SEQ ID NO: 26.

[SEQ ID NUMBER:26]
AAGCTTCGCGGATCCTTATCCTGGGTGACCACTTC-
ATTTTGGTTGATGCTAAGTCGCTCATAAATGGCAG-
TATGTGTTTTTCAAATACAGATGGGAATTCTACCCC-
GGGAAGACCCATGCACCCAGTTCTATTGCAGAAGC-
TTCGCGGATCCGCGTCCGCCCCGCGAGCACAGAG-
CCTCGCCTTTGCCGATCCGCCGCCCGTCCACACCC-
GCCGCCAGCTCACCATGGATGATGATATCGCCGCG-
CTCGTCGTCGACAACGGCTCCGGCATGTGCAAGG-
CCGGCTTCGCGGGCGACGATGCCCCCGGGCCGT-
CTTCCCCTCCATCGTGGGGCGCCCCAGGCACCAGG-
GCGTGATGGTGGGCATGGGTCAGAAGGATTCCGA-
ATTCTACCCCGGGTATGTGGGCGACGAGGCCCAGA-
GCAAGAGAGGCATCCTCACCCTGAAGTACCCCATC-
GAGCACGGCATCGTCACCAACTGGGACGACATGG-
AGAAAATCTGGCACCACACCTTCTACAATGAGCTG-
CGTGTGGCTCCCGAGGAGCACCCCGTGCTGCTGA-
CCGAGGCCCCCTGAACCCCAAGGCCAACCGCGA-
GAAGATGACCCAGATCATGTTTGAGACCTTCAAAA-
GCTTCGCGGATCCTGCTAAGCTGTGAGGCAGTGCA-
GGCTGGGACAGCCGACCTCCAGGTTGCGAAAAAC-
CTGGTTTCTGGGACCTCCCACCCCAGAGTAAAAGA-
ATTCTACCCCGGGCAGTTTGCTCAAGAATAAGCAG-

ACCTTTAAGCTTCGCGGATCCTTCATTCATCATGTC-
TAAAGCAATGCAGACATCCAGAAATTTTAGCCTCC-
CGCTATCCATTGTTCTGCTGACCTGAAGATCATTCA-
TAAATGGAGTCAAGTGTTCGTCAAAAAGAACTGG-
ATAATTTCTCCTTATAGATTGAATTCTACCCCGGGTC-
TGCTGACCTGAAGATCATTCATAAATGGAGTCAAG-
TGTTCGTCAAAAAGAACTGGATAATTTCTCCTTAT-
AGATTGCAGAACATGGTTCATTCCCAGTTGGTCTT-
CAATTTGTCTCACCACTTTAGGCTTCACAGCCCAA-
AGCTTCGCGGATCCCGGCAATTGCACTCGGAGTCG-
CCACAGCACACGGGAGTACCCTCGCAGGAGTAAA-
TGTTGGAGAACAGTATCAACAACTCAGAGAGGCT-
GCCACTGAGGCTGAGAAGCAAGAATTCTACCCCG-
GGTGCTGCGTCACTGCCCAAAACAAGTGGAAAGC-
TTCGCGGATCCTTATGAGTGCACTGCTCAGTACGC-
CAATGCCTATTGTTCACATGCTAATGGGTCAGGGA-
TTGTGCAGATACAAGTATCAGGGGTCTGGAAGAAG-
CCTTTATGTGTAGGGTATGAGAGAGTGGTTGTGAA-
GAGAGGAATTCTACCCCGGGACATGCTAATGGGTC-
AGGGATTGTGCAGATACAAGTATCAGGGGTCTGGA-
AGAAGCCTTTATGTGTAGGGTATGAGAGAGTGGTT-
GTGAAGAGAGAACTCTCTGCCAAGCCCATCCAGA-
GAGTTGAGCCTTGCACAAGCTTCGCGGATCCTTTA-
CTTGTCTGCGGCGCCTTGGGCGCCGTAGTCGAAC-
GCCCAGGTTATGCACCCGTTCACCTACAGATACAG-
CTGGTTAATACCAGGATAATTCCATCAAGAATTCTA-
CCCCGGGACAGGTGTTTACCCATTCATGTGGGGAG-
GAGCCTACTGCTTCTGCGACAAGCTTCGCGGATCC-
AAACCATTTGAATGGATGTCAATCCGACTCTACTGT-
TCCTAAAGGTTCCAGCGCAAAATGCCATAAGCACC-
ACATTCCCTTATACTGGAGATCCTCCATACAGCCAT-
GGAACAGTCTACTGTTGAATTCTACCCCGGGTGGA-
ACAGTCTACTGTTCCTAAAGGTTCCAGCGCAAAAT-
GCCATAAGCACCACATTCCCTTATACTGGAGATCCT-
CCATACAGCCATGGAACAGGAACAGGATACACCAT-
GGACACAGTCAAAAGCTTCGCGGATCCGCACCTCT-
GATCCAGACATGCAGTCGACCCTTAACTTTGACATC-
AAATCCACATGATGGATTTGATTTGCATATGCCATC-
AAGAAATATCTTAGACCTTGTAAAAATGTCTGGTTC-
CGAATTCTACCCCGGGCCCATTGATGGATAGATAGA-
TAGAATAGCACCTTGACTTCTCACCTGTTTTTAAGC-
TTCGCGGATCCTAGTTAGTTGCGACGGGTACGTCG-
TTAAAAGAATAGCTATCAGTCCAGGCCTGTATGGG-
AAGCCTTCAGGCTATGCTGCTACGATGCACCGTTA-
AAAGAATAGCTATCAGGAATTCTACCCCGGGGCT-
ATGCTGCTACGATGCACCGTTAAAAGAATAGCTATC-
AGTCCAGGCCTGTATGGGAAGCCTTCAGGCTATGC-
TGCTACGATGCACCGCGAGGGATTCTTGTGCTGCA-
AAAGCTTCGCGGATCCATGAAGTTGCTAGTTTCAA-
GCAGGCGTTGAGCAACCTAGCCCGACATGGAGAA-
TACGCACCGTTCGCACGGGTTCTGAATTTATCAGG-
GATTAACAACCTCGAACATGGACTCTATCGAATTCT-
ACCCCGGGTTCAGAAAACTGAAATCACACACAGT-
CAGACACTAGCCGTCCTCAGCCAGAAACGAGAAA-
AAAAGCTTCGCGGATCCAATTGATGATGAGCATGT-
CAGGCATTGATTGTATAAAATATCCCACAGGGCAGC-
TTATCACCCATGGAAGAGTGAGTGCAAAACATAAC-
GATGGGAACCTGAAAGATAGAAGCGAGAATTCTAC-
CCCGGGAACCTGTGCCCTTTCAGGTTGACTGTATAT-
TGTTCAAAGAAGTGGCAGCTGAATGCATGAAGAG-
GTACATTGGCACACCTTATGAGGGAATTGTAAGCTT-
CGCGGATCCTTTCAATATGCTGAAACGCGAGAGAA-
ACCGCGTGTCAACTGTTTCACAGTTGGCGAAGAG-
ATTCTCAAAAGGATTGCTTTCAGGCCAAGGACCCA-
TGAAATTGGTGATGGCTTTTATAGCGAATTCTACCC-
CGGGTTATGTGAGGACACAATGACCTACAAATGCC-
CCCGGATCACTGAGACGGAACCTGAAGACATTGA-
CTGTTGGTGCAATGAAGCTTCG CGGATCC

Size: 3143 bp

Once these nucleic acid sequences (or segments of the chimera) were identified, each segment was then prepared by PCR amplification. Synthetic chimeras were designed to produce PCR amplicons of different sizes (as indicated in FIG. 3) than the amplified fragments from the original pathogenic genome (to prevent that any contamination with simulant could create false positives).

Figure 5:
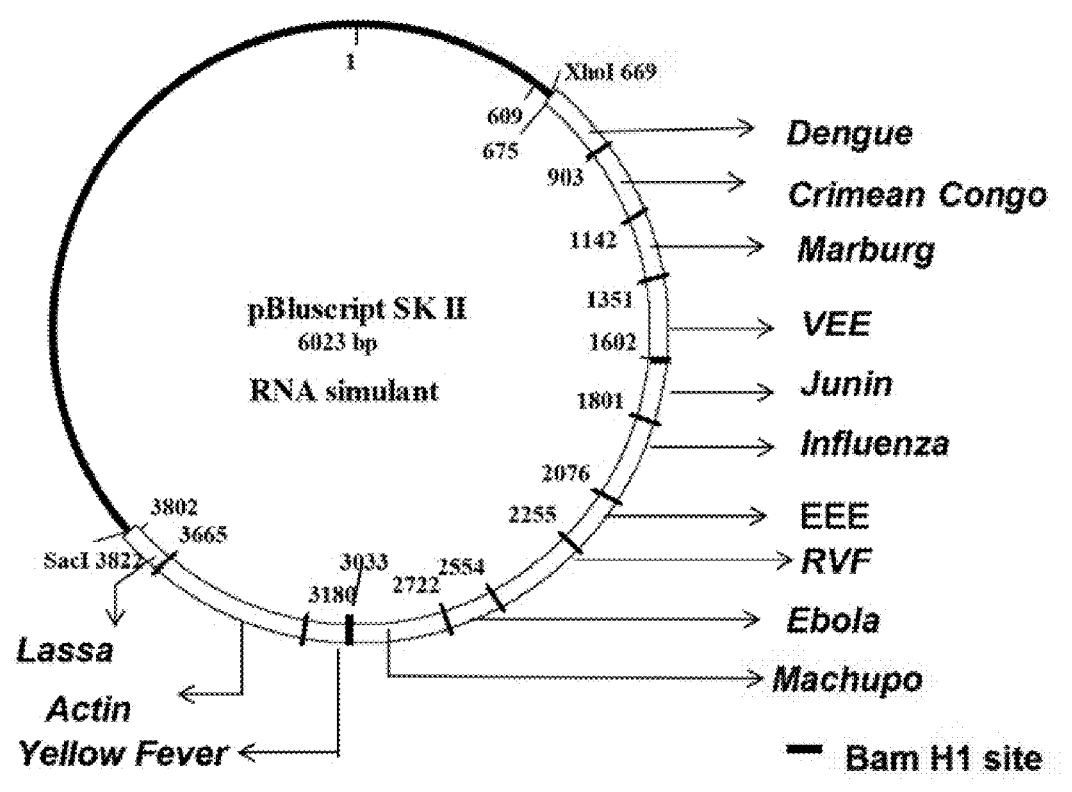

The chimera containing sequences corresponding to Biological Threat Agents having RNA genomes was inserted in the plasmid vector pBluscript SKII. A plasmid drawing comprising the whole chimera is described in FIG. 5, that shows the location in the plasmid vector of segments specific to each biothreat agent (separated by a Bam H1 restriction site), as well as the positions of restriction enzymes (SacI and XhoI) at the extremes of the insert.

The correct design and construction of the chimerical simulants (one for DNA agents and the other for RNA agents) was experimentally confirmed by releasing the inserts from the plasmid vector by digestion with one of the intersegment restriction enzymes (BamH1), performing multiplex PCR (using as primers the oligonucleotides underlined in sequences 1-26), and subsequent electrophoretic analysis shown in FIG. 6. The two vertical columns pointed by arrows in the gel in FIG. 6 correspond to nucleic acid fragments of the expected size (as indicated in FIG. 3) for agents whose genome is RNA (bands in column pointed by short downward arrow), and nucleic acids of the expected size (as indicated in FIG. 2) for agents whose genome is DNA (bands in column pointed by long downward arrow). The names of the agents are aligned to the corresponding fragments and their sizes are indicated (in base pairs, bp) at each side of the image representing the gel electrophoresis analysis.

REFERENCES

Sambrook, J., E. F. Fritsch, and T. Maniatis. 1989. Molecular Cloning: a Laboratory Manual, 2nd ed. Cold Spring Harbor Laboratory Press, Cold Spring Harbor, N.Y.

Bartlett J. M. S., Stirling D., eds. 2003. PCR Protocols, $2^{nd}$ ed. (Volume 226 in the series Methods in Molecular Biology.) Humana Press, Totowa, N.J.

Thompson J. D., Gibson T. J., Plewniak F., Jeanmougin F., and Higgins D. G. The CLUSTAL_X windows interface: flexible strategies for multiple sequence alignment by quality analysis tools. Nucleic Acids Res. 1997 Dec. 15; 25(24): 4876-82.

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention.

What is claimed is:

1. A method of detecting a biological threat agent, comprising the steps of:

(a) providing one or more samples suspected of containing one or more biological threat agents;

(b) performing a nucleic-acid based detection method to detect said one or more biological threat agents in said one or more samples;

(c) providing an additional sample containing a chimera comprising a plurality of segments, wherein each segment uniquely corresponds to a portion of the genome of a biological threat agent whose genome is RNA, and wherein said plurality of segments comprises a nucleic acid sequence comprising SEQ ID NO: 26; and (d) performing said nucleic-acid based detection method to detect said chimera in said additional sample as a positive control.

2. The method of claim 1, wherein the detection method comprises one or more nucleic acid probe methods.

3. The method of claim 1, wherein the detection method comprises PCR amplification methods.

* * * * *

SEQUENCE LISTING

<160> NUMBER OF SEQ ID NOS: 28

<210> SEQ ID NO 1
<211> LENGTH: 135
<212> TYPE: DNA
<213> ORGANISM: Francisella tularensis

<400> SEQUENCE: 1

| | | | | | | |
|---|---|---|---|---|---|---|
| ggatccgaca | agcttatggc | tttgcagcca | cttttgcaat | cgctgtgtga | gcccgggcag | 60 |
| cgaattccca | tttagatttt | tttgaatatg | cttgtaaaga | ccgaggctca | gaactaatcg | 120 |
| cagctacagc | acaag | | | | | 135 |

<210> SEQ ID NO 2
<211> LENGTH: 270
<212> TYPE: DNA
<213> ORGANISM: Yersinia pestis

<400> SEQUENCE: 2

| | | | | | | |
|---|---|---|---|---|---|---|
| ggatcctgaa | agcttgctgg | ggcgaaccca | cctcattggc | tatggcggcg | tcgcctgtca | 60 |
| cgtcctgttt | gagtgggata | aacgccacga | tgagttcgat | ctcgccatac | tggagaaagc | 120 |
| atggaaccag | ctcatcgcac | gccacgatat | gttgcgtatg | gtggttgccc | ggggcctgaa | 180 |
| ttctgacgat | cctcattatg | tcaatatcgg | tacggtgtta | gacaacgccg | actgacgccg | 240 |
| gagtatcaca | tcccgcgtga | cgatctgcgc | | | | 270 |

<210> SEQ ID NO 3
<211> LENGTH: 150
<212> TYPE: DNA
<213> ORGANISM: Burkholderia mallei

<400> SEQUENCE: 3

| | | | | | | |
|---|---|---|---|---|---|---|
| ggatccatga | agcttcattc | gtctttgcca | ttgccctgtc | atttgccgca | gcccgggtgc | 60 |
| tgaattcgtc | agcaatgcga | aatttacatc | cctacgcgag | ccttttgttt | ttaccgacct | 120 |
| gagtctgttc | agtcagttgt | tctcgcaccc | | | | 150 |

<210> SEQ ID NO 4
<211> LENGTH: 255
<212> TYPE: DNA
<213> ORGANISM: Bacillus anthracis

<400> SEQUENCE: 4

| | | | | | | |
|---|---|---|---|---|---|---|
| ggatccctca | agcttttaca | cgttttgctg | accaatctaa | gcctgcgttc | ttcgtaaatg | 60 |
| gttttgcagc | gaatgatccc | tcatcaacat | tacgtatttg | ggaacgtgtg | gatgattttg | 120 |
| gatatagtaa | tctagctcca | attgcccggg | agatgaattc | tacatctgcg | cgaatgatat | 180 |
| attggtttac | tgacgaggag | caaccgatta | agcgccgtag | cgttgatcgt | actgagcagt | 240 |
| ttgctaggga | tgttt | | | | | 255 |

<210> SEQ ID NO 5
<211> LENGTH: 165
<212> TYPE: DNA
<213> ORGANISM: Rickettsia sp.

-continued

<400> SEQUENCE: 5

```
ggatccggaa agcttagctg gtatcgctta ttttagaggt tatagagttc gcccgggtag      60
tgaattcgta aacctttatt ttttgatctt aatatttcta ctagaaccca aaacgtatcc    120
caagttcaaa gagctttact tttacctcaa gaagtaatac agtta                    165
```

<210> SEQ ID NO 6
<211> LENGTH: 240
<212> TYPE: DNA
<213> ORGANISM: Bacillus anthracis

<400> SEQUENCE: 6

```
ggatcctcta agcttgaaaa aggattggat ttcaagttgt actggaccga ttctcaaaat     60
aaaaaagaag tgatttctag tgataactta caattgccag aattaaaaca aaaatcttcg    120
aactcaagaa aacccgggga aagaattctc atctcctgaa aaatggagca cggcttctga    180
tccgtacagt gatttcgaaa aggttggacc tacggttcca gaccgtgaca atgatggaat    240
```

<210> SEQ ID NO 7
<211> LENGTH: 180
<212> TYPE: DNA
<213> ORGANISM: Coxiella burnetii

<400> SEQUENCE: 7

```
ggatccacta agcttcggat tgttacccaa cgaaaccttg cgtgaggcat tgaatcggga     60
attagatgaa gaagtgggac tgagtcctca cccgggtaca gaattccaat ggcggtgggt   120
tgattattgg tatccggtgg accacgtcgt tgagtttaag cgagacgttt atcagaaagt   180
```

<210> SEQ ID NO 8
<211> LENGTH: 225
<212> TYPE: DNA
<213> ORGANISM: Variola virus

<400> SEQUENCE: 8

```
ggatccataa agcttcggaa gagatgcagc accgtataca ccacccaatg gaatcattag     60
tatactctac accttatcct cagacacaga tatctaaaaa aataggtgat gatgcaactc   120
tatcatgtag tagaaataat ataccccggga cgtgaattcc aaacaaaatg tggaatagga   180
tacggagtat ccggacacac gtctgttgga gacgtcatct gttct                   225
```

<210> SEQ ID NO 9
<211> LENGTH: 195
<212> TYPE: DNA
<213> ORGANISM: Brucella sp.

<400> SEQUENCE: 9

```
ggatcctaga agcttaattg tgggccgatg gcgtcatcca tgtgctgggt gtcgggctgg     60
cgcttgccgg tgccattgcc atgctgttct atttcctccc gggaatcgaa ttctatgggc   120
gaccgcgcgc tgccctgct gctgttcgtg tggagcgtgg ctttcgtcgg catcatgctc    180
aaactgttca tgccg                                                    195
```

<210> SEQ ID NO 10
<211> LENGTH: 210
<212> TYPE: DNA
<213> ORGANISM: Escherichia coli

<400> SEQUENCE: 10

```
ggatccctga agcttgcgcg ctaacgcagg cctgaactca tcgtcggatg aattacaggc      60
ccagacgcgt attgccggaa tgcgctcaac gctggagcaa tatcacccgg ggcacgaatt     120
caagcgcaat actggccaac gctcagtatt caggggggta aaacgcgcta ccagaccagc     180
gaccgctcgt attgggatga tcagctacaa                                      210
```

<210> SEQ ID NO 11
<211> LENGTH: 90
<212> TYPE: DNA
<213> ORGANISM: Variola virus

<400> SEQUENCE: 11

```
tcattagtat actctacacc ttatcctcag acacagatat ctaaaaaaat aggtgatgat      60
gcaactctat catgtagtag aaataatata                                       90
```

<210> SEQ ID NO 12
<211> LENGTH: 2040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
ggatccgaca agcttatggc tttgcagcca cttttgcaat cgctgtgtga gcccgggcag      60
cgaattccca tttagatttt tttgaatatg cttgtaaaga ccgaggctca gaactaatcg     120
cagctacagc acaagggatc ctgaaagctt gctgggggcga acccacctca ttggctatgg    180
cggcgtcgcc tgtcacgtcc tgtttgagtg ggataaacgc cacgatgagt tcgatctcgc     240
catactggag aaagcatgga accagctcat cgcacgccac gatatgttgc gtatggtggt     300
tgcccgggc ctgaattctg acgatcctca ttatgtcaat atcggtacgg tgttagacaa      360
cgccgactga cgccggagta tcacatcccg cgtgacgatc tgcgcggatc catgaagctt     420
cattcgtctt tgccattgcc ctgtcatttg ccgcagcccg ggtgctgaat tcgtcagcaa     480
tgcgaaattt acatccctac gcgagccttt tgttttttacc gacctgagtc tgttcagtca    540
gttgttctcg cacccggatc cctcaagctt ttacacgttt tgctgaccaa tctaagcctg    600
cgttcttcgt aaatggtttt gcagcgaatg atccctcatc aacattacgt atttgggaac    660
gtgtggatga ttttggatat agtaatctag ctccaattgc ccgggagatg aattctacat    720
ctgcgcgaat gatatattgg tttactgacg aggagcaacc gattaagcgc cgtagcgttg    780
atcgtactga gcagtttgct agggatgttt ggatccggaa agcttagctg gtatcgctta    840
ttttagaggt tatagagttc gcccgggtag tgaattcgta aacctttatt ttttgatctt    900
aatatttcta ctagaaccca aaacgtatcc caagttcaaa gagctttact tttacctcaa    960
gaagtaatac agttaggatc ctctaagctt gaaaaggat tggatttcaa gttgtactgg    1020
accgattctc aaaataaaaa agaagtgatt tctagtgata acttacaatt gccagaatta    1080
aaacaaaaat cttcgaactc aagaaaaccc ggggaaagaa ttctcatctc ctgaaaaatg    1140
gagcacggct tctgatccgt acagtgattt cgaaaaggtt ggacctacgg ttccagaccg    1200
tgacaatgat ggaatggatc cactaagctt cggattgtta cccaacgaaa ccttgcgtga    1260
ggcattgaat cgggaattag atgaagaagt gggactgagt cctcacccgg gtacagaatt    1320
ccaatgcgg tgggttgatt attggtatcc ggtggaccac gtcgttgagt ttaagcgaga    1380
cgtttatcag aaagtggatc cataaagctt cggaagagat gcagcaccgt atacaccacc    1440
```

```
caatggaatc attagtatac tctacacctt atcctcagac acagatatct aaaaaaatag    1500
gtgatgatgc aactctatca tgtagtagaa ataatatacc cgggacgtga attccaaaca    1560
aaatgtggaa taggatacgg agtatccgga cacacgtctg ttggagacgt catctgttct    1620
ggatcctaga agcttaattg tgggccgatg gcgtcatcca tgtgctgggt gtcgggctgg    1680
cgcttgccgg tgccattgcc atgctgttct atttcctccc gggaatcgaa ttctatgggc    1740
gaccgcgcgc tgccectgct gctgttcgtg tggagcgtgg cttttcgtcgg catcatgctc    1800 aaactgttca tgccgggatc cctgaagctt gcgcgctaac gcaggcctga actcatcgtc    1860
ggatgaatta caggcccaga cgcgtattgc cggaatgcgc tcaacgctgg agcaatatca    1920
cccggggcac gaattcaagc gcaatactgg ccaacgctca gtattcaggg gggtaaaacg    1980
cgctaccaga ccagcgaccg ctcgtattgg gatgatcagc tacaaaagct tagaggatcc    2040

<210> SEQ ID NO 13
<211> LENGTH: 168
<212> TYPE: DNA
<213> ORGANISM: Zaire ebolavirus

<400> SEQUENCE: 13
aagcttcgcg gatcccggca attgcactcg gagtcgccac agcacacggg agtaccctcg      60
caggagtaaa tgttggagaa cagtatcaac aactcagaga ggctgccact gaggctgaga     120
agcaagaatt ctaccccggg tgctgcgtca ctgcccaaaa caagtgga                  168

<210> SEQ ID NO 14
<211> LENGTH: 179
<212> TYPE: DNA
<213> ORGANISM: Eastern equine encephalitis virus

<400> SEQUENCE: 14
aagcttcgcg gatcctttac ttgtctgcgg cgccttgggc gccgtagtcg aacgcccagg      60
ttatgcaccc gttcacctac agatacagct ggttaatacc aggataattc catcaagaat     120
tctaccccgg gacaggtgtt tacccattca tgtggggagg agcctactgc ttctgcgac     179

<210> SEQ ID NO 15
<211> LENGTH: 199
<212> TYPE: DNA
<213> ORGANISM: Junin virus

<400> SEQUENCE: 15
aagcttcgcg gatccgcacc tctgatccag acatgcagtc gacccttaac tttgacatca      60
aatccacatg atggatttga tttgcatatg ccatcaagaa atatcttaga ccttgtaaaa     120
atgtctggtt ccgaattcta ccccgggccc attgatggat agatagatag aatagcacct     180
tgacttctca cctgttttt                                                  199

<210> SEQ ID NO 16
<211> LENGTH: 209
<212> TYPE: DNA
<213> ORGANISM: Marburg virus

<400> SEQUENCE: 16
aagcttcgcg gatccatgaa gttgctagtt tcaagcaggc gttgagcaac ctagcccgac      60
atggagaata cgcaccgttc gcacgggttc tgaatttatc agggattaac aacctcgaac     120
atggactcta tcgaattcta ccccgggttc agaaaactga atcacacac agtcagacac      180 tagccgtcct cagccagaaa cgagaaaaa                                       209
```

```
<210> SEQ ID NO 17
<211> LENGTH: 229
<212> TYPE: DNA
<213> ORGANISM: Dengue virus type 1

<400> SEQUENCE: 17
aagcttcgcg gatcctttca atatgctgaa acgcgagaga aaccgcgtgt caactgtttc      60
acagttggcg aagagattct caaaaggatt gctttcaggc caaggaccca tgaaattggt     120
gatggctttt atagcgaatt ctaccccggg ttatgtgagg acacaatgac ctacaaatgc     180
ccccggatca ctgagacgga acctgaagac attgactgtt ggtgcaatg                 229

<210> SEQ ID NO 18
<211> LENGTH: 251
<212> TYPE: DNA
<213> ORGANISM: Venezuelan equine encephalitis virus

<400> SEQUENCE: 18
aagcttcgcg gatcctagtt agttgcgacg ggtacgtcgt taaaagaata gctatcagtc      60
caggcctgta tgggaagcct tcaggctatg ctgctacgat gcaccgttaa agaatagct     120 atcaggaatt ctaccccggg ggctatgctg ctacgatgca ccgttaaaag aatagctatc     180
agtccaggcc tgtatgggaa gccttcaggc tatgctgcta cgatgcaccg cgagggattc     240
ttgtgctgca a                                                          251

<210> SEQ ID NO 19
<211> LENGTH: 239
<212> TYPE: DNA
<213> ORGANISM: Crimean-Congo hemorrhagic fever virus

<400> SEQUENCE: 19
aagcttcgcg gatccaattg atgatgagca tgtcaggcat tgattgtata aaatatccca      60
cagggcagct tatcacccat ggaagagtga gtgcaaaaca taacgatggg aacctgaaag     120
atagaagcga gaattctacc ccgggaacct gtgcccttc aggttgactg tatattgttc     180
aaagaagtgg cagctgaatg catgaagagg tacattggca caccttatga gggaattgt     239

<210> SEQ ID NO 20
<211> LENGTH: 275
<212> TYPE: DNA
<213> ORGANISM: Influenza virus A

<400> SEQUENCE: 20
aagcttcgcg gatccaaacc atttgaatgg atgtcaatcc gactctactg ttcctaaagg      60
ttccagcgca aaatgccata agcaccacat tcccttatac tggagatcct ccatacagcc     120
atggaacagt ctactgttga attctacccc gggtggaaca gtctactgtt cctaaaggtt     180
ccagcgcaaa atgccataag caccacattc ccttatactg gagatcctcc atacagccat     240
ggaacaggaa caggatacac catggacaca gtcaa                                275

<210> SEQ ID NO 21
<211> LENGTH: 299
<212> TYPE: DNA
<213> ORGANISM: Rift valley fever virus

<400> SEQUENCE: 21
aagcttcgcg gatccttatg agtgcactgc tcagtacgcc aatgcctatt gttcacatgc      60
taatgggtca gggattgtgc agatacaagt atcaggggtc tggaagaagc ctttatgtgt     120
agggtatgag agagtggttg tgaagagagg aattctaccc cgggacatgc taatgggtca     180
```

```
gggattgtgc agatacaagt atcaggggtc tggaagaagc ctttatgtgt agggtatgag    240
agagtggttg tgaagagaga actctctgcc aagcccatcc agagagttga gccttgcac    299

<210> SEQ ID NO 22
<211> LENGTH: 311
<212> TYPE: DNA
<213> ORGANISM: Machupo virus

<400> SEQUENCE: 22
aagcttcgcg gatccttcat tcatcatgtc taaagcaatg cagacatcca gaaattttag     60
cctcccgcta tccattgttc tgctgacctg aagatcattc ataaatggag tcaagtgttc    120
gtcaaaaaga actggataat ttctccttat agattgaatt ctaccccggg tctgctgacc    180
tgaagatcat tcataaatgg agtcaagtgt tcgtcaaaaa gaactggata atttctcctt    240
atagattgca gaacatggtt cattcccagt tggtcttcaa tttgtctcac cactttaggc    300
ttcacagccc a                                                         311

<210> SEQ ID NO 23
<211> LENGTH: 137
<212> TYPE: DNA
<213> ORGANISM: Lassa virus

<400> SEQUENCE: 23
aagcttcgcg gatccttatc ctgggtgacc acttcatttt ggttgatgct aagtcgctca     60
taaatggcag tatgtgtttt tcaaatacag atgggaattc taccccggga agacccatgc    120
acccagttct attgcag                                                   137

<210> SEQ ID NO 24
<211> LENGTH: 147
<212> TYPE: DNA
<213> ORGANISM: Yellow fever virus

<400> SEQUENCE: 24
aagcttcgcg gatcctgcta agctgtgagg cagtgcaggc tgggacagcc gacctccagg     60
ttgcgaaaaa cctggtttct ggacctccc accccagagt aaagaattc taccccgggc      120 agtttgctca agaataagca gaccttt                                        147

<210> SEQ ID NO 25
<211> LENGTH: 485
<212> TYPE: DNA
<213> ORGANISM: Homo sapiens

<400> SEQUENCE: 25
aagcttcgcg gatccgcgtc cgccccgcga gcacagagcc tcgcctttgc cgatccgccg     60
cccgtccaca cccgccgcca gctcaccatg gatgatgata tcgccgcgct cgtcgtcgac    120
aacggctccg gcatgtgcaa ggccggcttc gcgggcgacg atgccccccg ggccgtcttc    180
ccctccatcg tggggcgccc caggcaccag ggcgtgatgg tgggcatggg tcagaaggat    240
tccgaattct accccgggta tgtgggcgac gaggcccaga gcaagagagg catcctcacc    300
ctgaagtacc ccatcgagca cggcatcgtc accaactggg acgacatgga gaaaatctgg    360
caccacacct tctacaatga gctgcgtgtg gctcccgagg agcacccgt gctgctgacc     420 gaggcccccc tgaaccccaa ggccaaccgc gagaagatga cccagatcat gtttgagacc    480
ttcaa                                                                485
```

<210> SEQ ID NO 26
<211> LENGTH: 3143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
aagcttcgcg gatccttatc ctgggtgacc acttcatttt ggttgatgct aagtcgctca    60
taaatggcag tatgtgtttt tcaaatacag atgggaattc taccccggga agacccatgc   120
acccagttct attgcagaag cttcgcggat ccgcgtccgc ccgcgagca cagagcctcg    180
cctttgccga tccgccgccc gtccacaccc gccgccagct caccatggat gatgatatcg   240
ccgcgctcgt cgtcgacaac ggctccggca tgtgcaaggc cggcttcgcg ggcgacgatg   300
cccccgggc cgtcttcccc tccatcgtgg ggcgcccag gcaccagggc gtgatggtgg    360
gcatgggtca gaaggattcc gaattctacc ccgggtatgt gggcgacgag ccccagagca   420
agagaggcat cctcaccctg aagtacccca tcgagcacgg catcgtcacc aactgggacg   480
acatggagaa atctggcac cacaccttct acaatgagct cgtgtggct cccgaggagc    540
accccgtgct gctgaccgag gcccccctga accccaaggc caaccgcgag aagatgaccc   600
agatcatgtt tgagaccttc aaaagcttcg cggatcctgc taagctgtga ggcagtgcag   660
gctgggacag ccgacctcca ggttgcgaaa aacctggttt ctgggacctc ccaccccaga   720
gtaaaagaat tctaccccgg gcagtttgct caagaataag cagacctta agcttcgcgg   780
atccttcatt catcatgtct aaagcaatgc agacatccag aaattttagc ctcccgctat   840
ccattgttct gctgacctga agatcattca taaatgagt caagtgttcg tcaaaaagaa    900
ctggataatt tctccttata gattgaattc taccccgggt ctgctgacct gaagatcatt   960
cataaatgga gtcaagtgtt cgtcaaaaag aactggataa tttctcctta tagattgcag  1020
aacatggttc attcccagtt ggtcttcaat ttgtctcacc actttaggct tcacagccca  1080
aagcttcgcg gatcccggca attgcactcg gagtcgccac agcacacggg agtaccctcg  1140
caggagtaaa tgttggagaa cagtatcaac aactcagaga ggctgccact gaggctgaga  1200
agcaagaatt ctaccccggg tgctgcgtca ctgcccaaaa caagtggaaa gcttcgcgga  1260
tccttatgag tgcactgctc agtacgccaa tgcctattgt tcacatgcta atgggtcagg  1320
gattgtgcag atacaagtat caggggtctg gaagaagcct ttatgtgtag ggtatgagag  1380
agtggttgtg aagagaggaa ttctaccccg ggacatgcta atgggtcagg gattgtgcag  1440
atacaagtat caggggtctg gaagaagcct ttatgtgtag ggtatgagag agtggttgtg  1500
aagagagaac tctctgccaa gcccatccag agagttgagc cttgcacaag cttcgcggat  1560
cctttacttg tctgcggcgc cttgggcgcc gtagtcgaac gcccaggtta tgcacccgtt  1620
cacctacaga tacagctggt taataccagg ataattccat caagaattct accccgggac  1680
aggtgtttac ccattcatgt ggggaggagc ctactgcttc tgcgacaagc ttcgcggatc  1740
caaaccattt gaatggatgt caatccgact ctactgttcc taaaggttcc agcgcaaaat  1800
gccataagca ccacattccc ttatactgga gatcctccat acagccatgg aacagtctac  1860
tgttgaattc taccccgggt ggaacagtct actgttccta aaggttccag cgcaaaatgc  1920
cataagcacc acattccctt atactggaga tcctccatac agccatgaa caggaacagg   1980
atacaccatg gacacagtca aaagcttcgc ggatccgcac tctgatcca gacatgcagt  2040
cgacccttaa ctttgacatc aaatccacat gatggatttg atttgcatat gccatcaaga  2100
```

-continued

```
aatatcttag accttgtaaa aatgtctggt tccgaattct accccgggcc cattgatgga   2160
tagatagata gaatagcacc ttgacttctc acctgttttt aagcttcgcg gatcctagtt   2220
agttgcgacg ggtacgtcgt taaaagaata gctatcagtc caggcctgta tgggaagcct   2280
tcaggctatg ctgctacgat gcaccgttaa aagaatagct atcaggaatt ctaccccggg   2340
ggctatgctg ctacgatgca ccgttaaaag aatagctatc agtccaggcc tgtatgggaa   2400
gccttcaggc tatgctgcta cgatgcaccg cgagggattc ttgtgctgca aaagcttcgc   2460
ggatccatga agttgctagt ttcaagcagg cgttgagcaa cctagcccga catggagaat   2520
acgcaccgtt cgcacgggtt ctgaatttat cagggattaa caacctcgaa catggactct   2580
atcgaattct accccgggtt cagaaaactg aaatcacaca cagtcagaca ctagccgtcc   2640
tcagccagaa acgagaaaaa aagcttcgcg gatccaattg atgatgagca tgtcaggcat   2700
tgattgtata aaatatccca cagggcagct tatcacccat ggaagagtga gtgcaaaaca   2760
taacgatggg aacctgaaag atagaagcga gaattctacc ccgggaacct gtgccctttc   2820
aggttgactg tatattgttc aaagaagtgg cagctgaatg catgaagagg tacattggca   2880
caccttatga gggaattgta agcttcgcgg atcctttcaa tatgctgaaa cgcgagagaa   2940
accgcgtgtc aactgtttca cagttggcga agagattctc aaaaggattg ctttcaggcc   3000
aaggacccat gaaattggtg atggctttta tagcgaattc taccccgggt tatgtgagga   3060
cacaatgacc tacaaatgcc cccggatcac tgagacggaa cctgaagaca ttgactgttg   3120
gtgcaatgaa gcttcgcgga tcc                                            3143

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaattctacc ccggg                                                       15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aagcttcgcg gatcc                                                       15
```